US005681549A

United States Patent [19]

McLaughlin et al.

[11] Patent Number: 5,681,549
[45] Date of Patent: Oct. 28, 1997

[54] MOUTHRINSE COMPOSITIONS

[75] Inventors: Kevin Thomas McLaughlin, Cincinnati; Stephen Joseph Hunter-Rinderle, Mason; William Gerald Hall, Cincinnati, all of Ohio

[73] Assignee: The Procter & Gamble Company, Cincinnati, Ohio

[21] Appl. No.: 634,029

[22] Filed: Apr. 17, 1996

Related U.S. Application Data

[63] Continuation of Ser. No. 258,151, Jun. 10, 1994.

[51] Int. Cl.⁶ .................. A61K 7/16; A61K 7/22
[52] U.S. Cl. ...................... 424/54; 424/49
[58] Field of Search ........................... 424/49–58

[56] References Cited

U.S. PATENT DOCUMENTS

| | | | |
|---|---|---|---|
| 3,164,524 | 1/1965 | Fand et al. | 167/93 |
| 3,864,472 | 2/1975 | Pensak et al. | 424/54 |
| 3,954,962 | 5/1976 | Prussin | 424/49 |
| 4,152,418 | 5/1979 | Pader | 424/50 |
| 4,154,815 | 5/1979 | Pader | 424/50 |
| 4,312,889 | 1/1982 | Melsheimer | 426/86 |
| 4,323,551 | 4/1982 | Parran | 424/54 |
| 4,472,373 | 9/1984 | Ryan | 424/54 |
| 4,476,107 | 10/1984 | Schmolka | 424/49 |
| 4,490,353 | 12/1984 | Crawford et al. | 424/52 |
| 4,540,567 | 9/1985 | Oneto et al. | 424/45 |
| 4,649,044 | 3/1987 | Gomi et al. | 424/49 |
| 4,661,342 | 4/1987 | Yamazaki et al. | 424/54 |
| 4,663,154 | 5/1987 | Ryan | 424/54 |
| 4,689,221 | 8/1987 | Kiyoshige et al. | 424/87 |
| 4,693,888 | 9/1987 | Miyahara et al. | 424/49 |
| 4,714,612 | 12/1987 | Nakamura et al. | 424/85 |
| 4,725,428 | 2/1988 | Miyahara et al. | 424/50 |
| 4,774,076 | 9/1988 | Gomi et al. | 424/49 |
| 4,816,261 | 3/1989 | Luebbe et al. | 424/65 |
| 4,897,261 | 1/1990 | Yamazaki et al. | 424/61 |
| 4,911,918 | 3/1990 | Kiyoshige et al. | 424/50 |
| 4,945,087 | 7/1990 | Talwar et al. | 514/60 |
| 4,954,335 | 9/1990 | Janchipraponvej | 424/70 |
| 4,961,923 | 10/1990 | Feyde | 424/49 |
| 4,992,276 | 2/1991 | Dills et al. | 424/439 |
| 4,994,262 | 2/1991 | Charbonneau et al. | 424/52 |
| 5,135,543 | 8/1992 | Chan et al. | 8/405 |
| 5,178,869 | 1/1993 | Ebine et al. | 424/401 |
| 5,211,940 | 5/1993 | Ishiguro et al. | 424/49 |
| 5,223,245 | 6/1993 | Ibrahim et al. | 424/49 |
| 5,256,823 | 10/1993 | Chan et al. | 564/284 |
| 5,284,648 | 2/1994 | White et al. | 424/49 |
| 5,292,527 | 3/1994 | Konopa | 424/54 |
| 5,298,238 | 3/1994 | Hussein et al. | 424/49 |
| 5,302,373 | 4/1994 | Giacin et al. | 424/49 |
| 5,330,749 | 7/1994 | Giacin et al. | 424/49 |
| 5,407,665 | 4/1995 | McLaughlin et al. | 424/58 |
| 5,560,906 | 10/1996 | Scodari et al. | |

FOREIGN PATENT DOCUMENTS

| | | | |
|---|---|---|---|
| 9408558 | 4/1994 | WIPO | |
| WO 94/08558 | 4/1994 | WIPO | A61K 7/16 |
| WO 94/18939 | 9/1994 | WIPO | A61K 7/22 |
| WO 94/27566 | 12/1994 | WIPO | A61K 7/26 |
| WO 95/17159 | 6/1995 | WIPO | A61K 7/22 |

OTHER PUBLICATIONS

Hall Chem. Abstr./Derwent Abstracts of WO/PCT 94 08558 Apr. 28, 1994.

Harth et al Chem. Abstr. 98:40 428 of Ger DE 31 13450 Oct. 7, 1982.

U.S. application No. 08/257,926, McLaughlin et al., filed Jun. 10, 1994.

*Primary Examiner*—Shep K. Rose
*Attorney, Agent, or Firm*—Mary Catherine Poland; Douglas C. Mohl; David K. Dabbiere

[57] ABSTRACT

The present invention relates to a mouthrinse and methods of use providing improved antimicrobial activity and thereby reducing oral bacteria, mouth malodor and further promoting oral health.

8 Claims, No Drawings

MOUTHRINSE COMPOSITIONS

This is a continuation of application Ser. No. 08/258,151, filed on Jun. 10, 1994.

TECHNICAL FIELD

The present invention relates to a mouthrinse and methods of use providing improved antimicrobial activity and thereby reducing oral bacteria, mouth malodor and further promoting oral health.

BACKGROUND OF THE INVENTION

Dental plaque is a mixed matrix of bacteria, epithelial cells, leukocytes, macro-phages and other oral exudate. Bacteria comprise approximately three-quarters of the plaque matrix. Any given sample of dental plaque could contain as many as 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

The bacteria found in plaque can secrete acids, enzymes and microtoxins which can cause caries, oral malodor and periodontal diseases such as gingivitis. The use of mouthrinses to reduce or eliminate the bacterial flora of the oral cavity has been recognized for some time. Examples of previous references include: U.S. Pat. No. 4,994,262, Feb. 19, 1991 to Charbonneau et al.; U.S. Pat. No. 4,923,685, May 8, 1990 to Wuelknitz et al.; U.S. Pat. No. 4,839,158, Jun. 13, 1989 to Michaels; U.S. Pat. No. 4,824,661, Apr. 25, 1989 to Wagner; U.S. Pat. No. 4,719,100, Jan. 12, 1988 to Frosch; U.S. Pat. No. 4,716,035, Dec. 29, 1987 to Sampathkumar; U.S. Pat. No. 4,606,911, Aug. 19, 1986 to Hayashi et al.; U.S. Pat. No. 4,525,343, Jun. 25, 1985 to Raaf, U.S. Pat. No. 4,323,551, Apr. 6, 1982 to Parran, Jr.; U.S. Pat. No. 4,312,889, Jan. 26, 1982 to Melsheimer; U.S. Pat. No. 4,152,418, May 1, 1979 to Pader; U.S. Pat. No. 4,082,841, Apr. 4, 1978 to Pader; U.S. Pat. No. 3,988,433, Oct. 26, 1976 to Benedict; U.S. Pat. No. 3,954,962, May 4, 1976 to Prussin; and U.S. Pat. No. 3,560,608, Feb. 2, 1971 to Griebstein et al.

In addition to the compositions set forth in the above-mentioned U.S. Patents, several additional references disclose mouthrinses for use in the oral cavity. See for example: Belgian Patent 776,425, published Jun. 8, 1972 to Imperial Chemical Industries Limited; Canadian Patent 1081-127, published Jul. 8, 1980; Japanese Kokai 54008-713, published Jan. 23, 1979; Japanese Kokai 49007-440, published Jan. 23, 1974; Soviet Union Patent 874-061, published Oct. 25, 1981 to Krasd Perfume Works and Soviet Union Patent Application 740-248, published Jun. 6, 1980 to Mosc Svoboda Cosmetics (similar to U.S. Pat. No. 3,591,675, Jul. 6, 1971 to Brillant).

While antimicrobials have long been used in oral mouthrinses, there is still a need for additional formulations which provide improved antimicrobial activity along with increased user acceptance.

The present invention relates to mouthrinse compositions combining specific mounts of a quaternary ammonium antimicrobial and a polyhydric alcohol to achieve improved antimicrobial activity. Although each of U.S. Pat. Nos. 5,256,823 and 5,135,543, Oct. 26, 1993 and Aug. 4, 1992 respectively, to Chan et al., U.S. Pat. No. 5,178,869, Jan. 12, 1993, to Ebine et al., U.S. Pat. No. 4,954,335, Sep. 4, 1990, to Janchipraponvej and U.S. Pat. No. 4,816,261, Mar. 28, 1989, to Luebbe et al. disclose combining quaternary ammonium compounds and polyhydric alcohols, none of these references require the incorporation of these components as described in the instant disclosure to arrive at the compositions and objectives of the present invention.

It is therefore an object of the present invention to provide improved mouthrinse compositions. It is a further object of the present invention to provide improved mouthrinse compositions with improved antimicrobial activity. A still further object of the present invention is to provide an effective method of treating or preventing plaque and related periodontal diseases such as gingivitis.

These objects and other objects will become more apparent from the detailed description that follows.

SUMMARY OF THE INVENTION

The present invention relates to a clear mouthrinse composition containing:

a.) from about 0.01% to about 0.5% of a quaternary ammonium compound;

b.) from about 5% to about 20% of a polyhydric alcohol selected from among the group consisting of propylene glycol, butylene glycol, hexylene glycol and mixtures thereof, and c.) an orally acceptable carrier wherein said composition contains less than about 1% of any anionic or nonionic surfactants and wherein the viscosity of said composition is below about 5 centipoise.

All levels and ratios are by weight of the total composition, unless otherwise indicated. Additionally, all measurements are made at 25° C. unless otherwise specified.

DETAILED DESCRIPTION OF THE INVENTION

The mouthrinse compositions of the present invention are preferably clear. By "clear" as used herein does not mean colorless, but means substantially lacking the presence of particles of sufficient size to scatter visible light as detected visually.

By the term "orally acceptable carrier," as used herein, means a suitable vehicle which can be used to apply, the present compositions to the oral cavity in a safe and effective manner.

The pH of those compositions herein described range from about 4.0 to about 9.5, with the preferred pH being from about 4.0 to about 9.0 and the most preferred pH being 4.5 to about 8.5.

The essential as well as optional components of the compositions of the present invention are described in the following paragraphs.

ESSENTIAL INGREDIENTS

Quaternary Ammonium Antimicrobial Agents

An essential component of the present invention is the quaternary ammonium antimicrobial agent.

Quaternary ammonium compounds are among the most common of the cationic antimicrobial agents. In oral compositions, they are highly effective in promoting oral hygiene by inhibiting or reducing the number of plaque forming bacteria. Quaternary ammonium antibacterial agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, Jun. 3, 1980 to Bailey which is incorporated herein by reference. The pyridinium compounds are the preferred quaternary ammonium compounds for use in the present invention, the most preferred being cetylpyridinium chloride, tetradecylpyridinium chloride or mixtures thereof. Quaternary ammonium antimicrobial agents are included in the present invention at levels of about 0.01% to about 0.5%, preferably from about 0.01% to below about 0.2%, more preferably from about 0.01% to about 0.15%.

Polyhydric Alcohols

Another essential ingredient of the present invention is the polyhydric alcohol. Polyhydric alcohols are best known for their solvent and humectant properties. These alcohols are soluble in water, alcohols, ethers and lower aliphatic hydrocarbons and also act to solubilize the flavoring agents of the present invention. The polyhydric alcohols useful in the present invention include those selected from among the group consisting of propylene glycol, butylene glycol, hexylene glycol and mixtures thereof.

The polyhydric alcohols comprise from about 5% to about 20% of the inventive compositions, preferably from about 10% to about 15%.

Water

Water is also present in the mouthrinse compositions of the present invention. Water comprises from about 50% to about 90%, preferably from about 70% to about 85% of the mouthrinse compositions described herein. These mounts of water include the free water which is added, plus that amount which is introduced with other materials such as with sorbitol. The water, used in the present invention should preferably be deionized, distilled, free of organic impurities and bacteria and substantially free of metal ions.

OPTIONAL COMPONENTS

The present invention may optionally include a water-soluble fluoride compound present in the composition in an amount sufficient to give a fluoride ion concentration in the composition at 25° C. of from about 0.0025% to about 5.0% by weight, preferably from about 0.005% to about 2.0% by weight when it is used to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Abrasives useful in abrading grinding and polishing teeth may also be optionally incorporated into compositions of the present invention. Typical dentally acceptable abrasives include insoluble calcium salts, alumina, silica, synthetic resins and mixtures thereof. Suitable silica abrasives are described in U.S. Pat. No. 5,176,900, herein incorporated by reference. Similarly, U.S. Pat. No. 4,623,536 discloses sodium bicarbonate, baking soda, as a mild abrasive and is herein incorporated by reference. Other compounds useful as abrasives are described in U.S. Pat. No. 5,176,901 which is also herein incorporated by reference. Mixtures of the above described abrasives may also be used.

Also desirable for inclusion in the compositions of the present invention are other stannous salts which will not inhibit the activity of the quaternary ammonium compound such as stannous pyrophosphate and stannous gluconate and other antimicrobials such as bis-biquanide salts, copper bisglycinate and nonionic antimicrobial salts. Also useful are enzymes, including endoglycosidase, papain, dextranase, mutanase and mixtures thereof. Such agents are disclosed in U.S. Pat. No. 2,946,725, Jul. 26, 1960, to Norris et al. and U.S. Pat. No. 4,051,234, Sep. 27, 1977 to Gieske et al., both of which are herein incorporated by reference.

Surfactants useful as optional components of the present invention include nonionic surfactants, betaines, zwitterionic surfactants or mixtures thereof. Suitable nonionic surfactants are described in U.S. Pat. No. 4,992,276, Feb. 12, 1991, Dills et al., incorporated herein by reference. Most preferred from among the nonionic surfactants are the poloxamer surfactants. A particularly preferred poloxamer is Poloxamer 407, which is sold under the tradename Pluronic F-127 by BASF-Wyandotte, Parsippany, N.J.

Betaine surfactants are also useful in the compositions of the present invention. Preferred betaine surfactants are disclosed in U.S. Pat. No. 5,180,577, Jan. 19, 1993, to Polefka et al., incorporated herein by reference. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amido-betaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

Zwitterionic surfactants, like betaines, carry both a charged acidic and a charged basic moiety on the same molecule. Preferred zwitterionic synthetic surfactants can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Zwitterionic surfactants suitable for use in the present invention are further described in U.S. Pat. No. 4,198,392, Apr. 15, 1980, to Juneja, incorporated herein by reference.

Another optional ingredient is a humectant. Humectants are well known in the art. The humectant may be a single agent or a mixture of compatible humectants In the present invention, suitable humectants include xylitol, glycerin and sorbitol as well as other polyhydroxy alcohols other than the required alcohols of the present invention. While it is feasible to use a combination of humectants, the preferred embodiment incorporates the use of a single humectant. Humectants provide from about 0% to about 55%, and most preferably from about 5% to about 20% of the herein described invention. The preferred humectants include glycerin and/or sorbitol.

The flavoring agent or a mixture of compatible flavoring agents represent still another optional ingredient of the present invention. Such flavoring agents are well known in the art. Suitable flavoring agents include: anise, cassia, clove, dihydroanethole, estragole, menthol, peppermint, oxanone, phenyl ethyl alcohol, sweet birch, thymol, eugenol, eucalyptol, wintergreen, spearmint, cinnamic aldehyde, menthone, alpha-ionone, ethyl vanillin, limonene, isoamylacetate, benzaldehyde, ethylbutyrate and many others. In the herein described compositions the flavoring agents comprise from about 0.01% to about 5.0%, preferably from about 0.05% to about 2.0% and most preferably from about 0.1% to about 1.0% of the herein described composition.

Another preferred nonessential component of the present invention is a cooling agent or a combination of cooling agents. Suitable cooling agents are those described in U.S. Pat. No. 4,136,163, Jan. 23, 1979, to Watson et al., U.S. Pat. No. 4,230,688, Oct. 28, 1980, to Rowsell et al. and U.S. Pat. No. 4,032,661, to Rowsell et al., all of which are herein incorporated by reference. Particularly preferred cooling agents are N-ethyl-p-menthane-3-carboxamide (WS-3 supplied by Sterling Organics), taught by the above incorporated U.S. Pat. No. 4,136,163 and N,2,3-trimethyl-2-isopropylbutanamide which is commercially available as WS-23 from Wilkinson Sword Limited and taught by the above incorporated U.S. Pat. No. 4,230,688. Another particularly preferred cooling agent is 3-1-menthoxypropane 1,2-diol (TK-10 supplied by Takasago Perfumery Co., Ltd., Tokyo, Japan). This material is described in detail in U.S. Pat. No. 4,459,425, Jul. 10, 1984 to Amano et al. and incorporated herein by reference.

Other optional components include, but are not limited to: coloring agents; sweeteners, including saccharin, dextrose, levulose, cyclamate and aspartate, along with many others; buffering systems such as benzoic acid and sodium benzoate, citric acid and sodium citrate, bicarbonates, peroxides, nitrate salts such as sodium and potassium nitrate and any other buffering system compatible with the invention's herein described essential components. These agents, if present, are included at levels of from about 0.01% to about 30%. Another optional component of the present invention is ethyl alcohol. Ethyl alcohol provides several functions when combined in the compositions of the present invention. Its inclusion can be, but is not limited to use as an additional antibacterial or as an astringent. Ethyl alcohol can be incorporated in the present invention at a level of less than about 40%, preferably less than about 10% and most preferably in concentrations of less than 2%.

EXAMPLES

The following examples further describe and demonstrate preferred embodiments within the scope of the present invention. The examples are given solely for illustration, and are not to be construed as limitation of this invention as many variations thereof are possible without departing from its spirit and scope.

Example I

A mouthrinse of the present invention is prepared by sequentially dissolving each of the following ingredients with agitation in a stainless steel or glass mixing tank containing the butylene glycol:

| Ingredients | % W/W |
| --- | --- |
| Butylene Glycol | 10.0000 |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye No. 1, 1.00% Solution (alc. free) | 0.0200 |
| Yellow Dye No. 5, 1.00% Solution | 0.0200 |

Examples II–VI are combinations made by incorporating the components using conventional mixing technology similar to that described in Example I.

Example II

| Ingredients | % of W/W |
| --- | --- |
| Propylene Glycol | 10.0000 |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye No. 1, 1.00% Solution (alc. free) | 0.0200 |
| Yellow Dye No. 5, 1.00% Solution | 0.0200 |

Example III

| Ingredients | % of W/W |
| --- | --- |
| Hexylene Glycol | 10.0000 |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye No. 1, 1.00% Solution (alc. free) | 0.0200 |
| Yellow Dye No. 5, 1.00% Solution | 0.0200 |

Example IV

| Ingredients | % of W/W |
| --- | --- |
| Hexylene Glycol | 5.0000 |
| Propylene Glycol | 5.0000 |

-continued

| Ingredients | % of W/W |
| --- | --- |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye, No. 1, 1.00% Solution (alc. free) | 0.0200 |
| Yellow Dye No. 5, 1.00% Solution | 0.0200 |

Example V

| Ingredients | % of W/W |
| --- | --- |
| Hexylene Glycol | 5.0000 |
| Butylene Glycol | 5.0000 |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye, No. 1, 1.00% Solution (alc. free) | 0.0200 |
| Yellow Dye No. 5, 1.00% Solution | 0.0200 |

Example VI

| Ingredients | % of W/W |
| --- | --- |
| Propylene Glycol | 5.0000 |
| Butylene Glycol | 5.0000 |
| Flavor | 0.1600 |
| Cetyl Pyridinium Chloride | 0.0500 |
| Water, USP Purified | 79.4315 |
| Poloxamer 407 | 0.2000 |
| Sodium Benzoate | 0.0540 |
| Benzoic Acid | 0.0045 |
| Sodium Saccharin | 0.0600 |
| Glycerin, USP | 10.0000 |
| Blue Dye, No. 1, 1.00% Solution (alc. free) | 0.0200 |
| Yellow Dye No. 5, 1.00% Solution | 0.0200 |

What is claimed is:

1. A clear mouthrinse composition comprising:

a.) from about 0.01% to below about 0.5% of a quaternary ammonium compound;

b.) from about 5% to about 20% of a polyhydric alcohol selected from among the group consisting of butylene glycol, hexylene glycol and mixtures thereof, and c.) an orally acceptable carrier wherein said composition contains less than about 1% of any anionic or nonionic surfactants and wherein the viscosity of said composition is below about 5 centipoise.

2. A mouthrinse composition according to claim 1 wherein said quaternary ammonium compound is selected from among the group consisting of cetyl pyridinium chloride, tetradecyl pyridinium chloride and mixtures thereof and is present at a level of from about 0.01% to below about 0.15%.

3. A mouthrinse composition according to claim 2 wherein said quaternary ammonium compound is cetyl pyridinium chloride.

4. A mouthrinse composition according to claim 3 which further comprises from about 5.0% to about 55% of a humectant selected from the group consisting of glycerin, sorbitol and mixtures thereof.

5. A mouthrinse composition according to claim 4 which further comprises from about 0% to about 20% of ethyl alcohol.

6. A mouthrinse composition according to claim 5 which further comprises a cooling agent selected form the group consisting of 3-1-methoxypropane 1,2-diol, N-ethyl-p-methane-3-carboxamide, N,2,3-trimethyl-2-isopropylbutanamide and mixtures thereof.

7. A method of inhibiting bacteria, plaque and related periodontal diseases which comprises rinsing the oral cavity with a safe and effective amount of the composition of claim 5.

8. A method of inhibiting bacteria, plaque and related periodontal diseases which comprises rinsing the oral cavity with a safe and effective amount of the composition of claim 6.

* * * * *